(12) United States Patent
Leveille et al.

(10) Patent No.: US 12,369,926 B2
(45) Date of Patent: Jul. 29, 2025

(54) COMPUTER-ASSISTED SURGERY SYSTEM AND METHOD FOR ORIENTING A KNEE IMPLANT

(71) Applicant: ORTHOSOFT ULC, Montreal (CA)

(72) Inventors: Catherine Leveille, Montreal (CA); Benoit Pelletier, Montreal (CA); Bruno Falardeau, Verdun (CA); Karine Duval, Montreal (CA)

(73) Assignee: ORTHOSOFT ULC, Montreal (CA)

( * ) Notice: Subject to any disclaimer, the term of this patent is extended or adjusted under 35 U.S.C. 154(b) by 0 days.

(21) Appl. No.: 18/533,530

(22) Filed: Dec. 8, 2023

(65) Prior Publication Data

US 2024/0108359 A1 Apr. 4, 2024

Related U.S. Application Data

(60) Division of application No. 17/104,004, filed on Nov. 25, 2020, now Pat. No. 11,871,937, which is a continuation of application No. 16/013,282, filed on Jun. 20, 2018, now Pat. No. 10,874,405.

(60) Provisional application No. 62/522,398, filed on Jun. 20, 2017.

(51) Int. Cl.
  *A61B 17/15*    (2006.01)
(52) U.S. Cl.
  CPC .................. *A61B 17/155* (2013.01)
(58) Field of Classification Search
  CPC ..... A61B 17/15; A61B 17/151; A61B 17/154; A61B 17/155
  See application file for complete search history.

(56) References Cited

U.S. PATENT DOCUMENTS

| | | | | |
|---|---|---|---|---|
| 8,265,790 | B2* | 9/2012 | Amiot | A61B 17/155 606/88 |
| 10,874,405 | B2* | 12/2020 | Leveille | A61B 17/155 |
| 11,871,937 | B2* | 1/2024 | Leveille | A61B 17/155 |
| 2005/0149041 | A1* | 7/2005 | McGinley | A61B 17/155 606/88 |
| 2005/0234466 | A1* | 10/2005 | Stallings | A61B 17/15 606/88 |
| 2005/0261699 | A1* | 11/2005 | Neubauer | A61B 90/11 606/96 |
| 2008/0195109 | A1* | 8/2008 | Hunter | A61B 17/155 606/88 |

(Continued)

FOREIGN PATENT DOCUMENTS

| | | |
|---|---|---|
| DE | 10309493 A1 | 9/2004 |
| EP | 1302167 A2 | 4/2003 |

(Continued)

*Primary Examiner* — Eric S Gibson
(74) *Attorney, Agent, or Firm* — NORTON ROSE FULBRIGHT CANADA LLP

(57) ABSTRACT

A reference jig comprises a base adapted to be secured to a distal end of a bone. An adjustment mechanism has a bracket, one or more rotational joints operatively mounting the bracket to the base, whereby the bracket is rotatable in two or more rotational degrees of freedom relative to the base, and one or more translational joints. A landmark alignment unit is operatively connectable to the bracket by the at least one translational joint, the landmark alignment unit having a bone alignment component configured to be aligned with at least one bone landmark.

6 Claims, 9 Drawing Sheets

(56) References Cited

U.S. PATENT DOCUMENTS

| | | | | |
|---|---|---|---|---|
| 2009/0248044 A1* | 10/2009 | Amiot | ............... | A61B 17/155 |
| | | | | 606/130 |
| 2011/0208093 A1* | 8/2011 | Gross | .................... | A61B 90/10 |
| | | | | 600/587 |
| 2013/0060253 A1* | 3/2013 | Couture | ................ | A61B 90/50 |
| | | | | 606/88 |
| 2013/0073067 A1* | 3/2013 | Amiot | ................ | A61B 17/155 |
| | | | | 700/97 |
| 2016/0278938 A1* | 9/2016 | Goble | ............... | A61B 17/1675 |
| 2019/0053813 A1* | 2/2019 | Leveille | ............... | A61B 17/155 |
| 2019/0254682 A1* | 8/2019 | Amiot | .................. | A61B 34/20 |
| 2021/0077121 A1* | 3/2021 | Leveille | ................ | A61B 34/20 |
| 2024/0108359 A1* | 4/2024 | Leveille | .............. | A61B 17/155 |

FOREIGN PATENT DOCUMENTS

| | | |
|---|---|---|
| EP | 3415103 A1 | 12/2018 |
| WO | 2011127477 A1 | 10/2011 |

\* cited by examiner

COMPUTER-ASSISTED SURGERY SYSTEM AND METHOD FOR ORIENTING A KNEE IMPLANT

CROSS-REFERENCE TO RELATED APPLICATION

The present application is a divisional of U.S. patent application Ser. No. 17/104,004, filed on Nov. 25, 2020, which is a continuation of U.S. patent application Ser. No. 16/013,282, filed on Jun. 20, 2018 and which claims the priority of U.S. Patent Application No. 62/522,398, filed on Jun. 20, 2017 and incorporated herein by reference.

FIELD OF THE APPLICATION

The present application relates to computer-assisted surgery systems for instance using inertial sensors and, more particularly, to instrumentation used for guiding bone alterations in knee arthroplasty for the subsequent placement of a femoral and/or tibial implant.

BACKGROUND OF THE ART

Tracking of surgical instruments or tools is an integral part of computer-assisted surgery (hereinafter CAS). The tools are tracked for position (x,y,z coordinates) and/or orientation (phi, theta, rho angles) in such a way that information pertaining to bodily parts is obtained. The information is then used in various interventions (e.g., orthopedic surgery, neurological surgery) with respect to the body, such as bone alterations, implant positioning, incisions and the like during surgery. In particular, in the context of knee arthroplasty, an operator may require information relating to an orientation of cut blocks and cut guide relative to the distal end of the femur, to ensure adequate implant positioning to avoid or minimize any varus or valgus.

Inertial sensors such as accelerometers are commonly used for the tracking of surgical instruments. Some inertial sensors may be limited to outputting orientation tracking along two degrees of freedom (DOF) only, and/or an output of some inertial sensors may be without positional tracking. Accordingly, specific steps must be taken during surgery to provide the operator with the necessary navigation parameters in spite of the inherent two DOF limit or orientation-only limitation of some inertial sensors.

SUMMARY OF THE APPLICATION

It is therefore an aim of the present application to provide a novel method for performing alterations to a distal end of a femur in knee arthroplasty.

Therefore, in accordance with a first embodiment of the present disclosure, there is provided a reference jig comprising: a base adapted to be secured to a distal end of a bone; an adjustment mechanism having a bracket, at least one rotational joint operatively mounting the bracket to the base, whereby the bracket is rotatable in at least two rotational degrees of freedom relative to the base, and at least one translational joint; and a landmark alignment unit operatively connectable to the bracket by the at least one translational joint, the landmark alignment unit having a bone alignment component configured to be aligned with at least one bone landmark.

Further in accordance with the first embodiment, the bracket has for instance at least one abutment surface adapted to abut distal aspects of the bone.

Still further in accordance with the first embodiment, the bone alignment component is for instance a posterior abutment adapted to abut posterior aspects of the bone.

Still further in accordance with the first embodiment, the bracket has for instance at least one abutment surface adapted to abut distal aspects of the bone, a plane of the at least one abutment surface being perpendicular to a plane of the posterior abutment.

Still further in accordance with the first embodiment, the posterior abutment is for instance a condylar abutment adapted to abut against posterior aspects of condyles.

Still further in accordance with the first embodiment, a first rotational axis of the at least one rotational joint is for instance generally parallel to an anterior-posterior axis of the bone.

Still further in accordance with the first embodiment, a second rotational axis of the at least one rotational joint is for instance generally parallel to a medio-lateral axis of the bone.

Still further in accordance with the first embodiment, the bone alignment component has for instance a jaw supporting a pair of ends separated from one another for positioning the bone between.

Still further in accordance with the first embodiment, the bracket has for instance at least one abutment surface adapted to abut distal aspects of the bone, a plane of the at least one abutment surface being parallel to a line passing through the ends of the jaw.

Still further in accordance with the first embodiment, the jaw is for instance a transepicondylar line jaw.

Still further in accordance with the first embodiment, the at least one translational joint includes for instance a pair of slots in the bracket, and a pair of rails slidingly received in the slots and connected to the bone alignment component.

Still further in accordance with the first embodiment, an inertial sensor unit is for instance mounted to the base.

Still further in accordance with the first embodiment, the base has for instance a receptacle for releasably receiving the internal sensor unit in a known geometric relation.

Still further in accordance with the first embodiment, the base has for instance a spike adapted to be received in the bone.

In accordance with a second embodiment of the present disclosure, there is provided an assembly comprising: the reference jig as described above; a cut block having a cut slot releasably connected to the reference jig so as to be displaceable with the bracket in the at least two rotational degrees of freedom; at least one inertial sensor unit connected to at least one of the reference jig and the cut block to track a variation of orientation of the cut slot relative to the bone.

Still further in accordance with the second embodiment, one said inertial sensor unit is for instance connected to the reference jig, and another said inertial sensor unit connected to the cut block.

In accordance with a third embodiment of the present disclosure, there is provided a cut guide comprising: a bone anchor adapted to be received in a bone and project beyond a resected bone plane; a base having defining an underside with a sliding plane adapted to be laid against the resected bone plane; at least one rotational joint operatively mounting the bone anchor to the base, whereby the bracket is rotatable in a rotational degree of freedom while sliding on the resected bone plane, and an inertial sensor unit mounted to the base for determining an orientation of the resected bone plane.

Further in accordance with the third embodiment, at least one translational joint and a landmark alignment unit are for instance operatively connectable to the bracket by the at least one translational joint, the bone landmark alignment unit having a bone alignment component configured to be aligned with at least one bone landmark.

Still further in accordance with the third embodiment, the bone alignment component is for instance a posterior abutment adapted to abut posterior aspects of the bone.

Still further in accordance with the third embodiment, the posterior abutment is for instance a condylar abutment adapted to abut against posterior aspects of condyles.

Still further in accordance with the third embodiment, the at least one translational joint includes for instance a slot in the base, and a ball at the bone anchor, the ball and slot forming the at least one rotational joint and the at least one rotational joint.

Still further in accordance with the third embodiment, a bracket is for instance provided, a translational joint is for instance between the bracket and the base for translational movement of the bracket relative to the base in a direction generally parallel to the resected bone plane, and a sizing boom is for instance on the bracket.

Still further in accordance with the third embodiment, a scale is for instance formed between the bracket and the base at the translational joint.

In accordance with a fourth embodiment of the present disclosure, there is provided a method for creating a femoral coordinate system comprising: securing a reference jig at a distal end of a femur, the reference jig supporting an inertial sensor unit programmed with a known geometrical relation with respect to a femoral landmark; orienting the reference jig to be in aligned with one of a posterior condylar plane of the femur and a transepicondylar line of the femur; recording movements of the femur for tracking by the inertial sensor unit; and obtaining a femoral coordinate system defined by a femoral axis including the femoral landmark, a center of rotation of the femur and an alignment with the one of the posterior condylar plane of the femur and of the transepicondylar line of the femur.

In accordance with a fifth embodiment of the present disclosure, there is provided a system for validating a distal cut of a femur comprising: a processor unit; and a non-transitory computer-readable memory communicatively coupled to the processing unit and comprising computer-readable program instructions executable by the processing unit for: tracking a femoral coordinate system with a first inertial sensor unit of a computer-assisted surgery (CAS) system secured to the femur, receiving readings of a second inertial sensor unit of the computer-assisted surgery (CAS) as supported by a guide coplanar against the distal cut, determining an orientation of a plane of the distal cut in the femoral coordinate system, and validating the orientation with a planned orientation of the distal cut.

DESCRIPTION OF THE PREFERRED EMBODIMENTS

Figure 1:
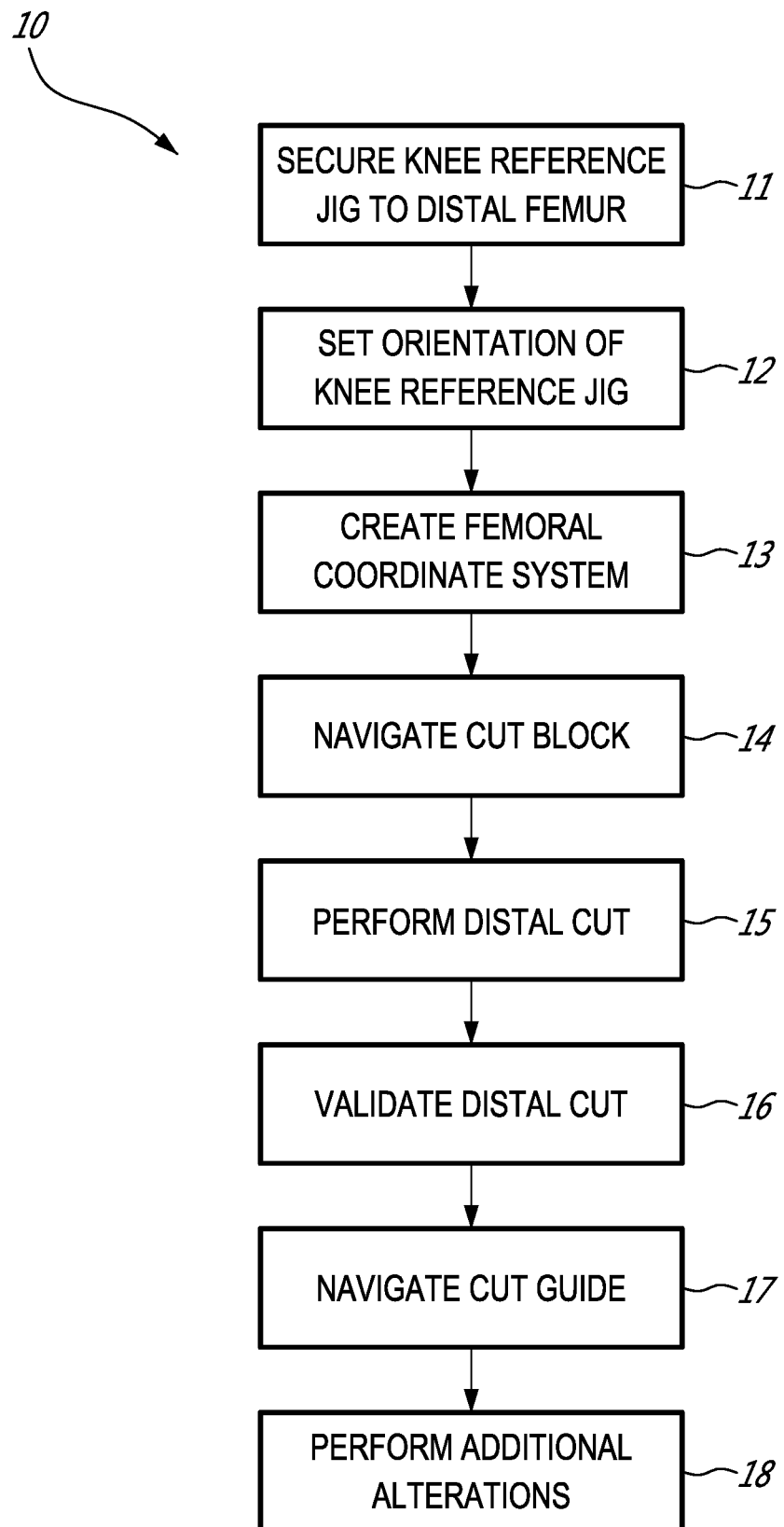
FIG. 1 is a flow chart of a method for performing alterations to a distal end of a femur in knee arthroplasty in accordance with the present disclosure, using inertial sensors of a computer-assisted surgery system.
Figure 2:
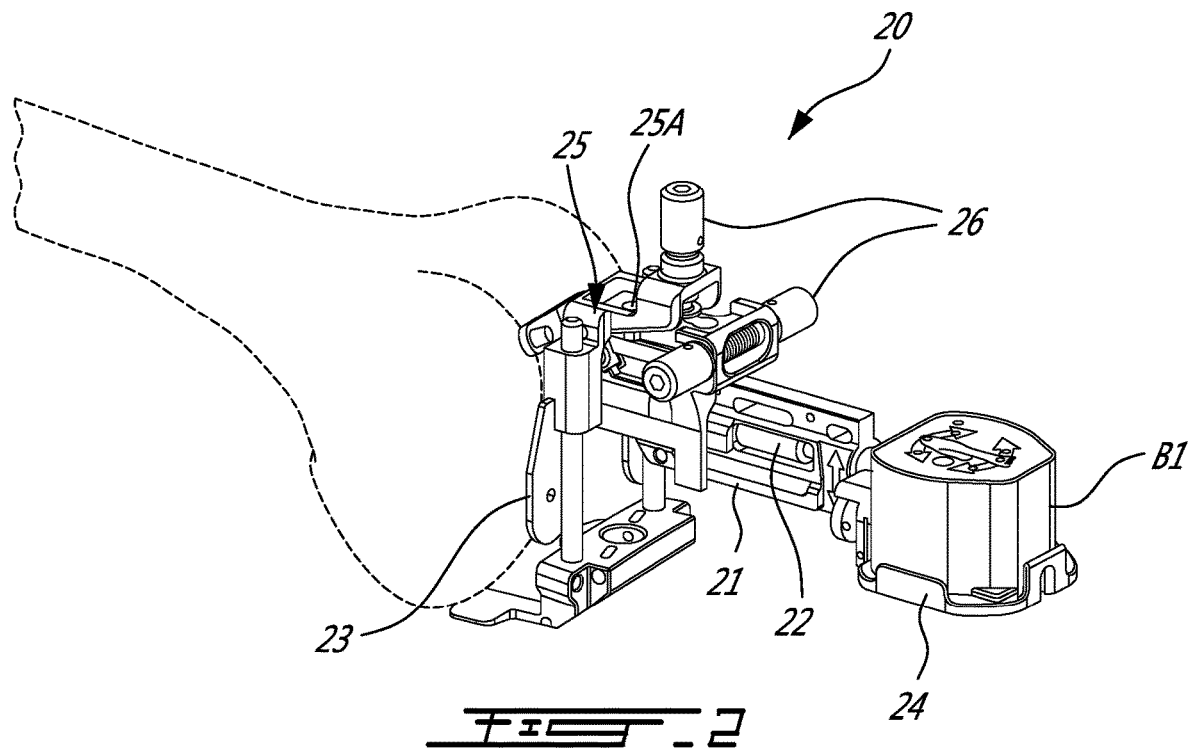
FIG. 2 is a perspective view of a knee reference jig in accordance with a first embodiment of the present disclosure, as mounted to a distal femur with alignment with a condylar plane.
Figure 3:
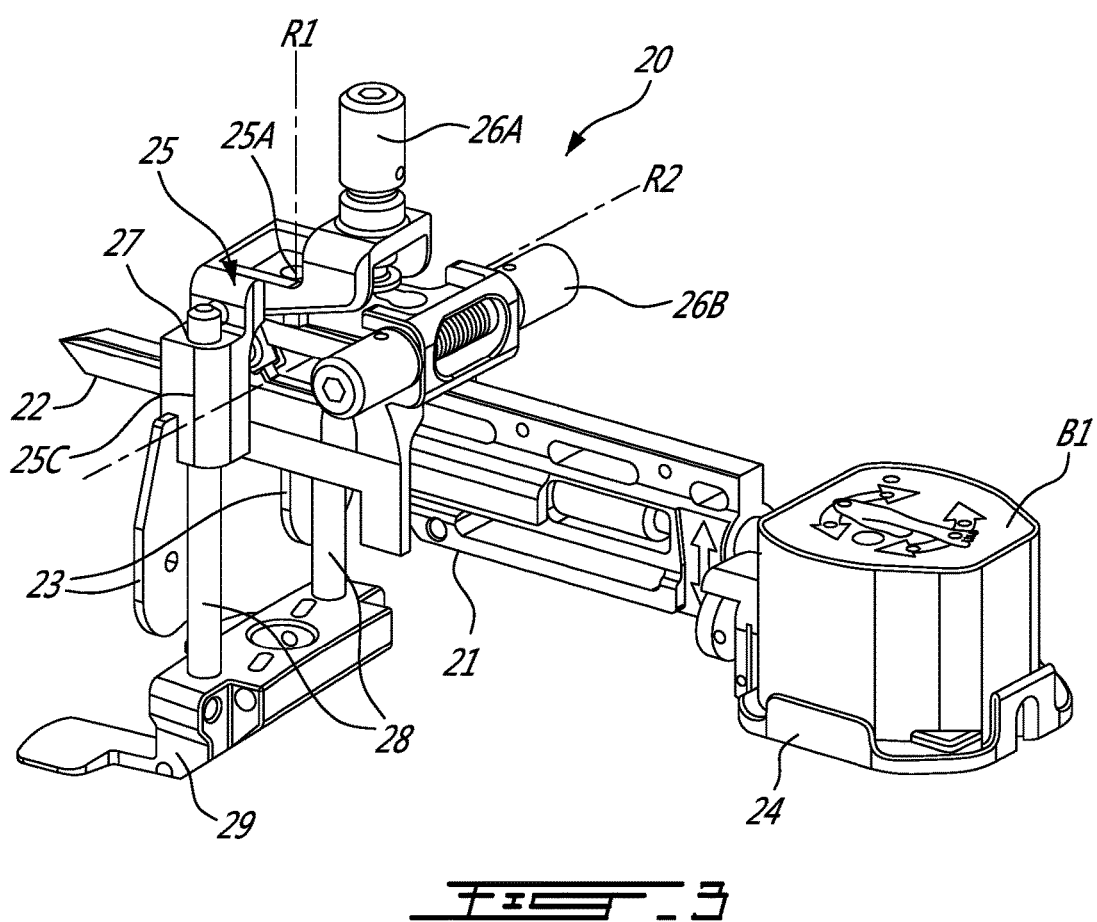
FIG. 3 is a perspective view of the knee reference jig of FIG. 2, as detached from the femur.
Figure 4:
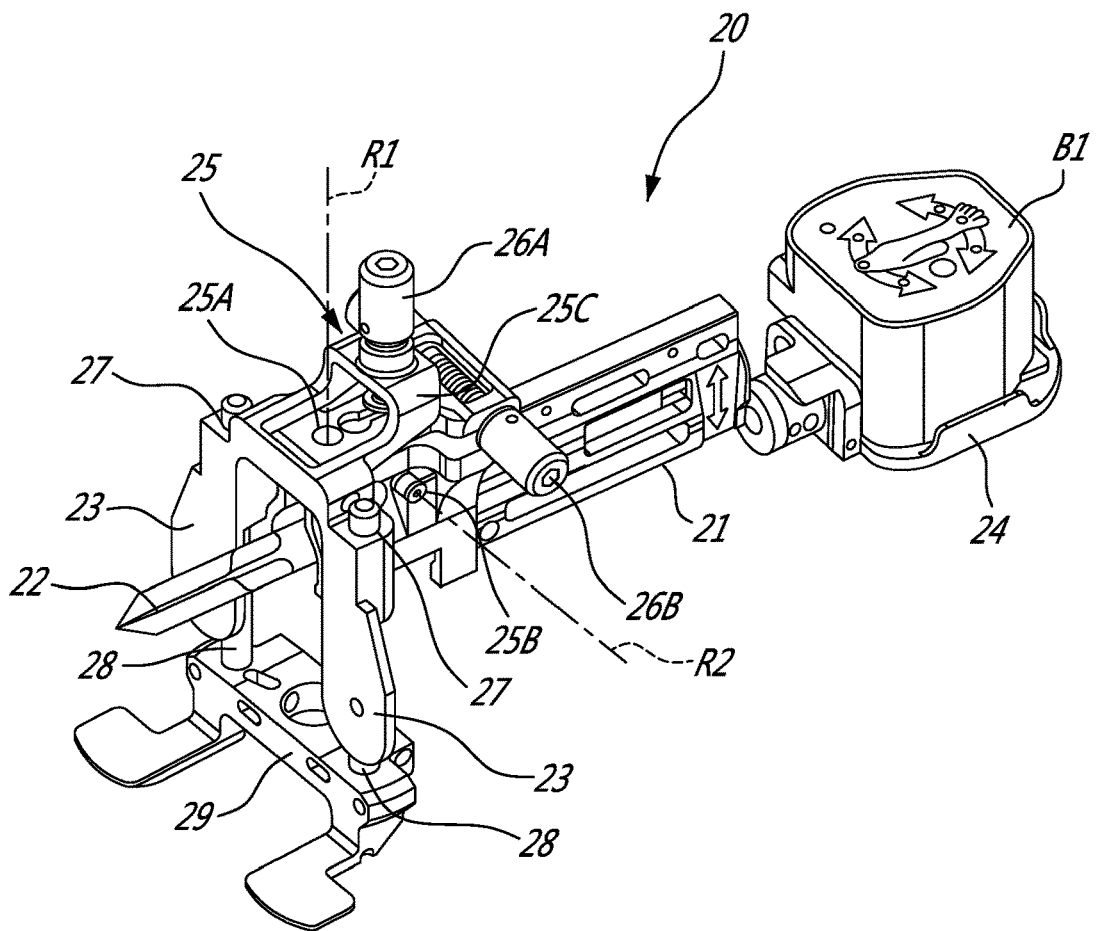
FIG. 4 is another perspective view of the knee reference jig of FIG. 2, as detached from the femur.
Figure 5:
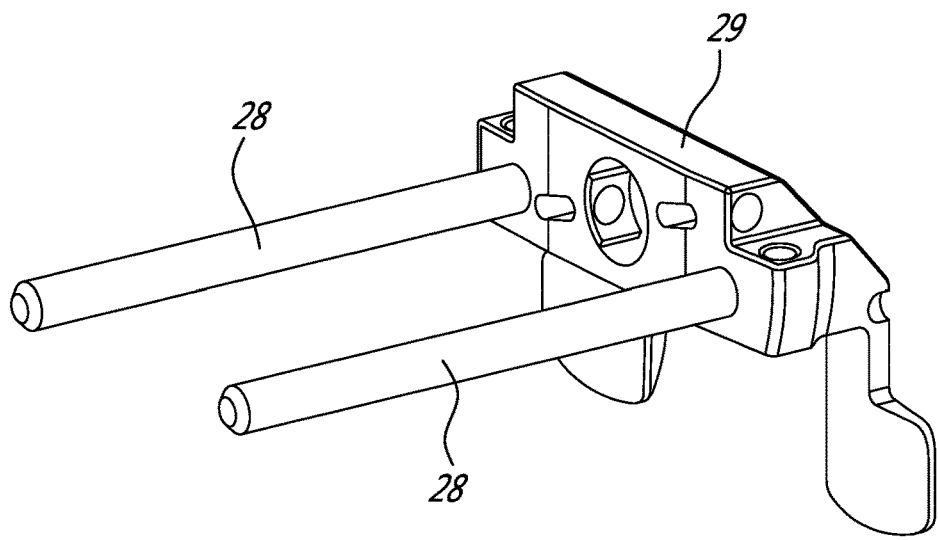
FIG. 5 is a perspective view of a condylar abutment of the knee reference jig of Fig.

Referring to FIG. 1, a method for performing alterations to a distal end of a femur in knee arthroplasty, using for instance inertial sensors of a computer-assisted surgery (CAS) system, is shown at 10. The alterations may be cuts and holes for a femoral knee implant to then be implanted at the distal end of the femur, at a position and orientation decided by the operator, through guidance of a CAS system in making bone alterations for receiving the femoral knee implant. As per convention, the distal end of the femur is the knee end of the femur, whereas the proximal end of the femur is the femoral head end of the femur. The method 10 guides the operator in performing the alterations on the distal end of the femur. The method is described with reference to 11-18 of FIG. 1, all representing steps of groups of steps, and with reference to hardware and electronic components, shown starting at FIG. 2.

According to 11, a knee reference jig is attached to the distal end of the femur. The knee reference jig may be as shown at 20 in FIGS. 2-5, or as shown as 30 in FIGS. 6-8, as detailed hereinafter. The knee reference jig may be attached to be located at a mechanical axis entry point of the distal end of the femur. A pin may then serve as a joint for movement of the knee reference jig 20 or 30 relative to the distal end of the femur. Other types of knee reference jigs may also be used, with the knee reference jigs 20 and 30 provided as examples. The knee reference jig 20 or 30 are used in such a way that the tools during the procedure are consistently aligned with selected bone landmarks throughout the procedure.

According to 12, an orientation of the knee reference jig 20/30 is set relative to the distal end of the femur. In other words, the knee reference jig 20/30 has its position and orientation fixed relative to the distal end of the femur, using for example screw(s) to pin the jigs 20/30 to the bone once an appropriate orientation is attained. The position of the knee reference jig 20/30 may be defined as being at the mechanical axis entry point, whereas its orientation can be set by abutments with bone landmarks. In an embodiment, the knee reference jig may be aligned with Whiteside's line.

In another embodiment, the knee reference jig 20 is aligned with the condyles, and more particularly with the posterior plane of the condyles. The posterior plane may be perpendicular to the plane in which lie the distal-most points of the condyles, and may include the posterior-most points of the condyles. In another embodiment, the knee reference jig 30 is aligned with the transepicondylar axis, i.e., the line between the most medial and lateral prominences of the epicondyles.

According to 13, a femoral coordinate system is created (also known as femoral frame of reference). The femoral coordinate system is a virtual coordinate system, i.e., virtually tracked, that is in register with physical landmarks of the femur. The virtual femoral coordinate system is therefore representative of the femur, with hardware components then tracked as a function of the femoral coordinate system to determine their orientation. To create the femoral coordinate system, the devices used in the procedure, such as the jigs 20 and 30, are equipped with an inertial sensor unit B1 so as to be in a fixed relation with the femur, and movements of the femur are made while recorded by the fixed inertial sensor unit B1. The inertial sensor unit B1 is an electronic component of the computer-assisted surgery (CAS) system, and outputs a signal representative of an orientation of the unit B1. The inertial sensor unit B1 and/or the CAS system may be programmed with geometrical data and preset virtual orientations, for the output of the inertial sensor unit B1 to be representative of an arrangement between the inertial sensor unit B1 and the femur, as described below.

Still in 13, the femoral coordinate system may include a mechanical axis of the femur, as well as an orientation of the jigs 20/30 relative to the desired landmark (e.g., Whiteside's line, posterior plane of the condyles, transepicondylar axis, etc). The mechanical axis of the femur may be determined from the movements that are used by the CAS system to identify a position of the center of rotation of the femoral head, and the programmed data of the geometrical relation of the inertial sensor unit B1 on the knee reference jig 20/30, enabling the CAS system to determine the entry point of the mechanical axis at the distal femur. For example, the inertial sensor unit B1 incorporates at least one accelerometer and at least one gyroscope and employs the method as described in U.S. Pat. No. 9,901,405, incorporated herein by reference.

Figure 9:
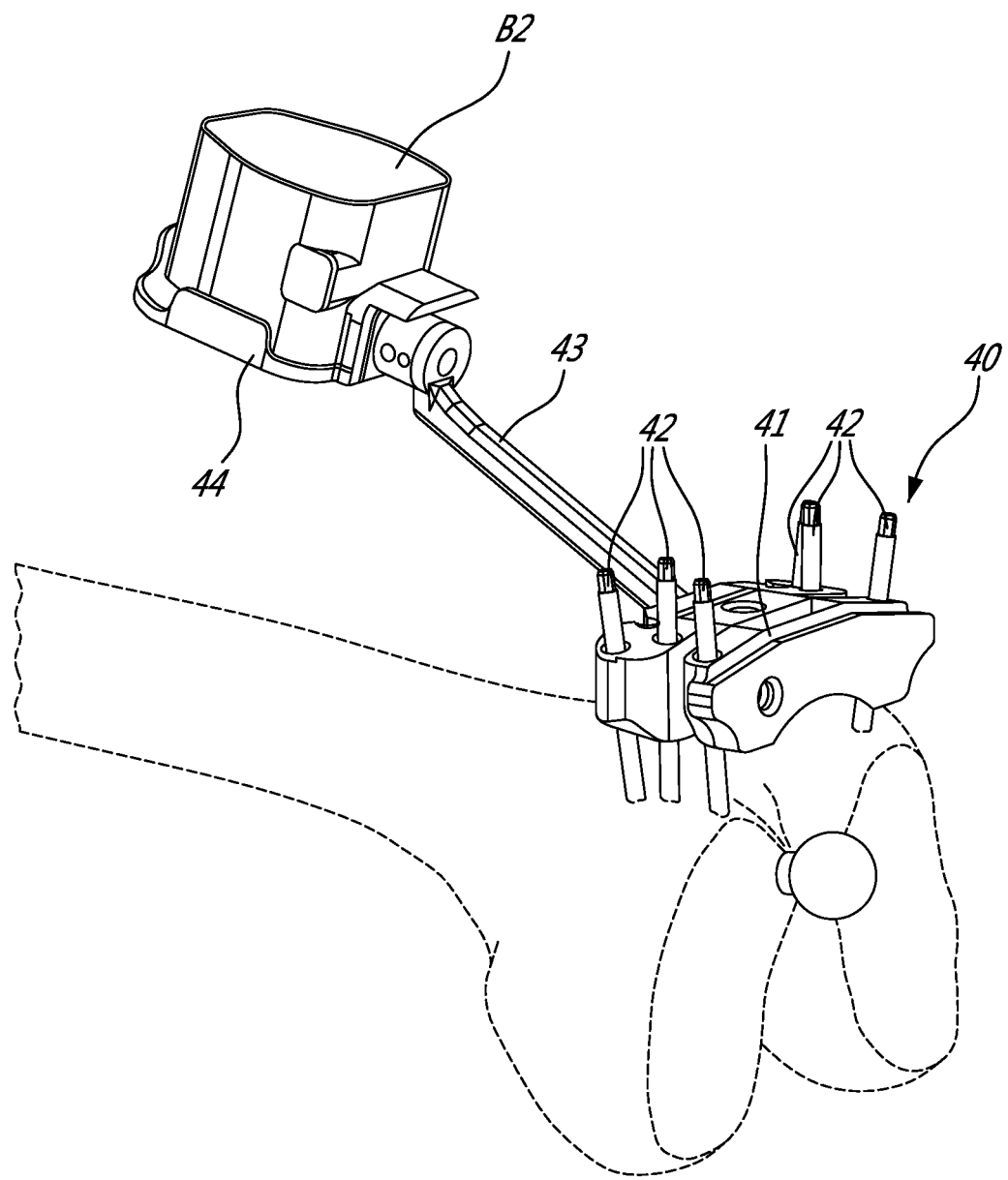
FIG. 9 is a perspective view of a cut block in accordance with the present disclosure, as mounted to the distal femur after distal cut.

According to 14, a cut block is navigated. Examples of cut block navigations are for instance described in U.S. patent application Ser. No. 13/035,264, and in U.S. Pat. No. 8,718,820, both incorporated herein by reference. The cut block, for example shown in one possible configuration as 40 in FIG. 9, is attached to the knee reference jig 20/30. The cut block 40 is "navigated", i.e., its orientation in the femoral coordinate system is tracked via the inertial sensor unit B1 and another inertial sensor unit B2 integrally connected to the cut block 40, as orientation adjustments via the knee reference jig 20/30. According to an embodiment, the cut block 40 may be displaced in two rotational degrees of freedom (DOF) with respect to a base of the knee reference jig 20/30, one of the rotational DOFs being representative of an anterior-posterior axis of the femur for varus/valgus adjustment, and the other of the rotational DOFs being generally aligned with a medio-lateral axis of the femur, for flexion/extension adjustment. Once a desired orientation is reached for a plane of the cut block 40, the cut block 40 may be pinned to the femur, for the distal cut to be made. The plane of the cut block 40 may be that of the cut slot of the cut block 40 adapted to receive a saw blade and may consequently correspond to the eventual distal cut.

The cut block 40 may have another inertial sensor unit, B2, secured to it, with the geometrical relation between the cut block 40 and the inertial sensor unit B2 being programmed in the inertial sensor unit B2, for the output of the inertial sensor unit B2 to be representative of the plane of the cut block 40. In such an arrangement, the inertial sensor units B1 and B2 are paired, for the inertial sensor unit B1 to track the femoral frame of reference while the inertial sensor unit B2 tracks the orientation adjustments of the cut block 40 relative to the femur. However, in another embodiment, it is contemplated to use a single inertial sensor unit, as described hereinafter. Moreover, the femoral coordinate system may be transferred to the inertial sensor unit B2 of the cut block 40 when the latter is fixed to the bone, for this inertial sensor unit B2 to become the main tracking reference of the CAS system tracking the femur via the femoral coordinate system, as the reference jig 20/30 and inertial sensor unit B1 may be detached from the femur for the distal cut to be effected, while the cut block 40 remains attached to the femur.

According to 15, the distal cut is performed, using the cut block 40. To perform the distal cut, the knee reference jig 20/30 may be removed from attachment to the femur. Any appropriate tool may be used for the distal cut, such as flat surgical saw blades. The distal cut is therefore oriented as desired by the preceding actions from the operator, including the orientation aligned with the Whiteside's line, posterior plane of the condyles, and/or transepicondylar axis, as desired.

According to 16, the distal cut may be validated. A knee cutting guide 50 as in FIGS. 10-13 may be used for the validation, with an inertial sensor unit B3 thereon. This knee cutting guide 50 may be dedicated to navigating the distal cut plane, or may supplementally be used for other functions, including planning the anterior cut, sizing the implant, navigating the pin holes, as described herein. For instance, the inertial sensor unit B3 may be in communication with the inertial sensor unit B2 on the cut block 40, for the readings of the inertial sensor unit B3 to be as a function of the femoral coordinate system tracked by the inertial sensor unit B2. The inertial sensor unit B3 may be the inertial sensor unit B1, programmed to perform the operations related to the knee cutting guide 50, or may be another inertial sensor unit B3. The inertial sensor units B1, B2 and B3 may in some instance be the same and transferred via dead reckoning to preserve their reference to the virtual femoral coordinate system.

The knee cutting guide 50 is laid flat on the distal cut, and is therefore constrained from rotating in one rotational DOF. The planar movements of the knee cutting guide 50 along the distal cut allow a determination of the orientation of the plane of the distal cut relative to the femoral coordinate system, and hence its validation as it may be compared to a planned orientation (i.e., as per the preceding steps). If the orientation of the distal cut must be corrected, an orientation of the cut block 40 may be adjusted via the inertial sensor unit B2, with a repeat of 14, 15 and 16, for example. This may require the reinstallation of the reference jig 20/30.

According to 17, the cut guide 50 is navigated, i.e., its position and orientation relative to the femoral coordinate system is selected based on its tracking, for the operator to determine the orientation of addition femoral alterations, such as pin placement, and various planar cuts, such as anterior cut, posterior cut, posterior chamfer and/or anterior chamfer, as a function of the implant that will be used. The cut guide 50 may be connected to a pin A with ball head (shown throughout FIGS. 9-13) located at the mechanical axis entry point, and forming a joint with the cut guide 50, allowing its movement. Sizing data may also be obtained. As the femoral coordinate system incorporates known landmarks, such as Whiteside's line, posterior plane of the condyles, and/or transepicondylar axis, etc, the operator can plan the additional femoral alterations by placing the cut guide 50 as a function of the known landmarks. The cut guide 50 may serve to place a pair of pins that will be used as landmarks for the placement of a femoral finishing guide, by which other planes may be cut.

According to 18, these additional alterations are performed, for the implant to be implanted. In an embodiment, the additional alterations include the placement of pin landmarks for a femoral finishing guide to be placed on the distal cut to perform additional cuts, such as the cuts defining the anterior condyle plane, the posterior condyle plane, the posterior chamfer and the anterior chamfer.

Referring to FIGS. 2-5, the knee reference jig 20 is shown in greater detail. The knee reference jig 20 is configured to orient itself with the condyles (a.k.a., posterior referencing), and is therefore used if the operator selects condylar alignment. The jig 20 has a base 21 that defines the structure of the jig 20, as the base 21 supports other components of the jig 20. A spike 22 or pin projects from the base 21, and is sized so as to be received in a hole drilled in the distal femur at the mechanical axis entry point. In an embodiment, the spike 22 may be an integral part of and/or immovable with respect to the base 21. Therefore, when the spike 22 is in the drilled hole, the jig 20 is at the mechanical axis entry point. The base 21 has an abutment plane, herein shown as a pair of abutment surfaces 23, for the distal aspects of the condyles. A single abutment surface 23 may also be present, for instance large enough to contact both condyles. The abutment surfaces 23 abut against the distal surfaces (a.k.a., aspects) of the condyles (i.e., medial and lateral condyles) when the spike 22 is received in the drilled hole. The base 21 also has a receptacle 24, for receiving the inertial sensor unit B1. The receptacle 24 is shaped for receiving the inertial sensor unit B1, such that any preset virtual orientation or like calibration data programmed into the inertial sensor unit B1 is aligned with physical parts of the jig 20, such as the abutment plane of the abutment surface(s) 23 and the spike 22.

An adjustment mechanism 25 is also operatively connected to the base 21, by a pair of rotation joints aligned with axes R1 and R2. The adjustment mechanism 25 has pivots 25A and 25B by which bracket 25C can rotate relative to the base 21. The cut block 40 may be releasably attached to the jig 20 to the bracket 25C for concurrent rotation with it. The other pivot 25B may be present as well, to form a second rotational joint relative to the base 21. The cut block 40 may be connected to the adjustment mechanism in other ways as well, including onto slots 27 or rails 28. The adjustment mechanism 25 has a pair of knobs 26 (concurrently referred to as 26, but shown as 26A and 26B), the knobs 26 operating rotational joints featuring the pivots 25A and 25B, respectively aligned with the anterior-posterior (AP) axis (knob 26A) and with the medio-lateral (ML) axis (knob 26B) when the jig 20 is attached to the femur in the manner described above. The rotational joints may be of the self-locking type, in that they hold the orientation to which they are adjusted. The bracket 25C is therefore displaceable in two rotational DOFs relative to the base 21. The knobs 26 allow minute or micro orientation adjustments. The base 21 may further define a pair of parallel slots 27 for slidingly receiving the rails 28, in a translational DOF. A landmark alignment unit is provided, as a condylar abutment 29 supported by the rails, such that the condylar abutment 29 may be brought closer or further to the base 21. The condylar abutment 29 defines a condylar plane, configured to come into contact with posterior aspects of the medial and lateral condyles. Hence a surface of the condylar abutment 29 serves as a bone alignment component. According to an embodiment, the condylar plane of the condylar abutment 29 and the abutment plane of the abutment surface(s) 23 are perpendicular to one another. The abutment surface(s) 23, the bracket 25C, the rails 28 and the condylar abutment 29 may all rotate concurrently relative to the base 21, and the rotations may be fine-tuned by the knobs 26A and 26B, about the AP axis and the ML axis, respectively.

Securing the knee reference jig 20 to the distal femur according to 11 of FIG. 1 entails inserting the spike 22 in the hole drilled at the mechanical axis entry point. In an embodiment, the jig 20 is manually oriented such that the condylar plane of the condylar abutment 29 contacts the posterior aspects of the condyles. The base 21 may then be driven into the hole of the femur 20, with the penetration adjusted until the abutment plane of the base 21 is against at least one of the distal aspects of the condyles. The depth of penetration may be adjusted to allow some play resulting in the abutment against the medial condyle and the lateral condyle. Alternatively or additionally, the knob 26A may be rotated to cause an adjustment of the orientation of the abutment plane about the anterior-posterior axis relative to the base 21 and bone. Likewise, the knob 26B may be rotated to cause an adjustment of the orientation of the abutment plane about the medio-lateral axis relative to the base 21 and bone. Setting the orientation as in 12 of FIG. 1 may require rotating the base 21 on itself, i.e., relative to the spike 22, and translating the condylar abutment 29 until the condylar abutment 29 comes into contact with the posterior aspects of both the medial and lateral condyles. However, in one embodiment, the rotation of the base 21 may not be required as it was performed initially before the base 21 was driven into the femur. The knee reference jig 20 is thus oriented with the posterior plane of the condyles.

The femoral coordinate system may be created by the appropriate kinematics as described in 13 of the method 10, using the known geometry between the inertial sensor unit B1 in the jig 20 and the preset virtual calibration in the inertial sensor unit B1. The known geometry may provide a position for the mechanical entry point via the spike 22, while the kinematics may be used to set the mechanical axis passing through the femoral head center. This may be done once the base 21 is driven into the femur, before or after the steps of adjusting the orientation via the knobs 26A and 26B.

Therefore, when the cut block 40 is assembled to the jig 20 via the connector 25A, on the bracket 25C or rails 28, the orientation of the cut block 40 in the femoral coordinate system (featuring the afore-mentioned landmarks) may be known as the connection geometry between the jig 20 and the cut block 40 is known.

Consequently, when placed on the femur, at the mechanical axis entry point, the jig 20 may have its base 21 fixed to the femur, and thus the inertial sensor unit B1 fixed. The abutment plane of the jig 20, defined by the abutment surface(s) 23, may be displaceable in two rotational DOFs relative to the base 21, via the knobs 26A and 26B. The knob 26A may adjust a varus-valgus orientation via a joint aligned with the anterior-posterior axis of the femur, while the knob 26B may adjust a flexion-extension orientation via a joint aligned with the medio-lateral axis of the femur. When the jig 20 is abutted as desired, the bracket 25C of the jig 20 may be in a baseline orientation, which may then be recorded by the inertial sensor unit B2 on the cut block 40. Parts of the jig 20 may then be removed to allow additional rotations of the cut block 40 relative to the femur via the knobs 26A and 26B, without having the abutment surface(s) 23 and condylar abutments 29 impeding.

When properly mounted to the distal femur, the jig 20 may therefore have joints providing two rotational DOF about the AP axis and the ML axis when the, and one translational DOF, in a direction generally parallel to the AP axis. This arrangement allows for the adjustment of the cutting block 40, as fixed to the adjustment mechanism 25, in varus-valgus and flexion-extension. It is also contemplated to switch the positioning of the joints around, for instance to allow rotation about the cranial-caudal axis.

Figure 6:
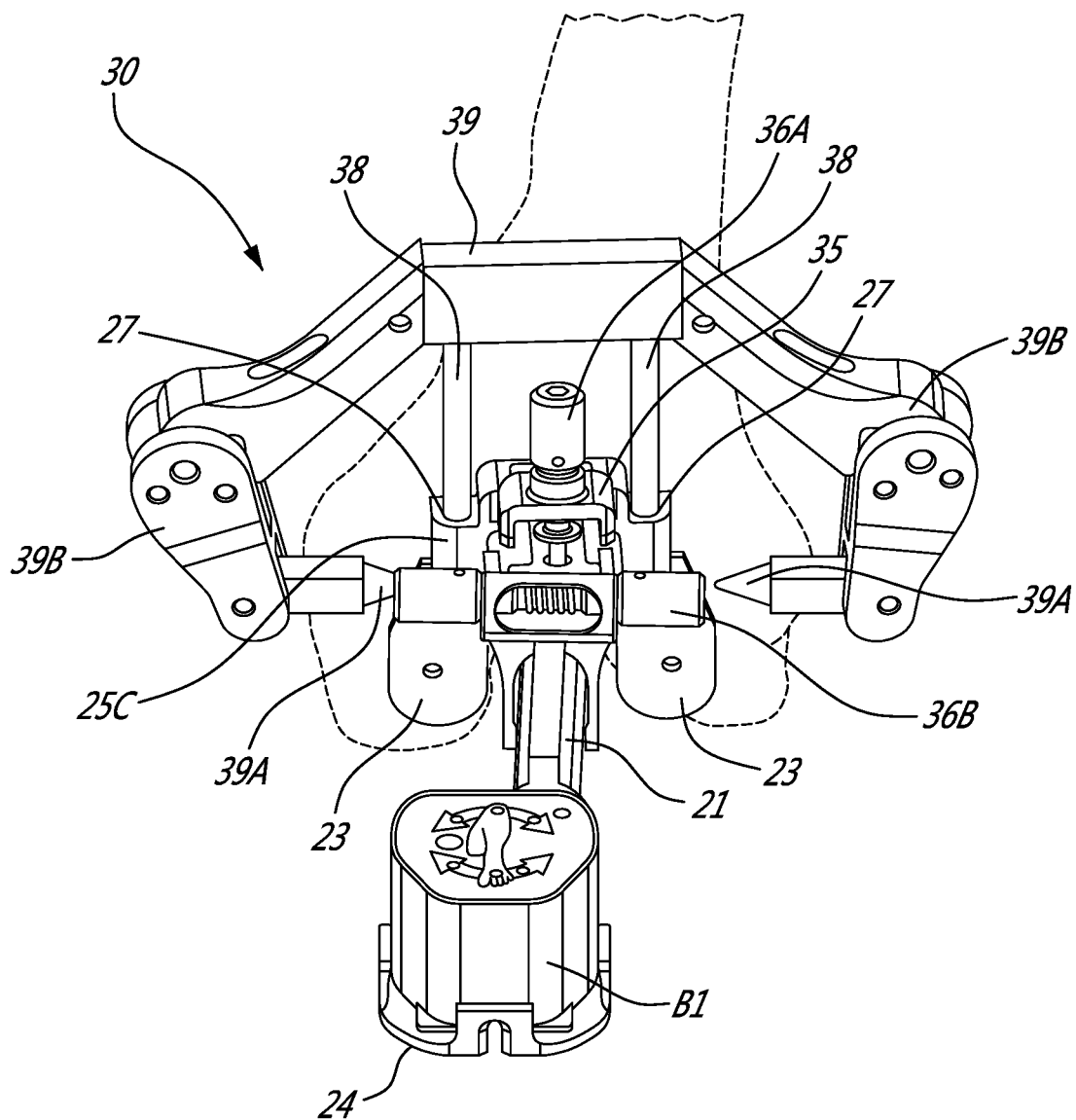
FIG. 6 is a perspective view of a knee reference jig in accordance with a second embodiment of the present disclosure, as mounted to a distal femur, for transepicondylar line alignment
Figure 7:
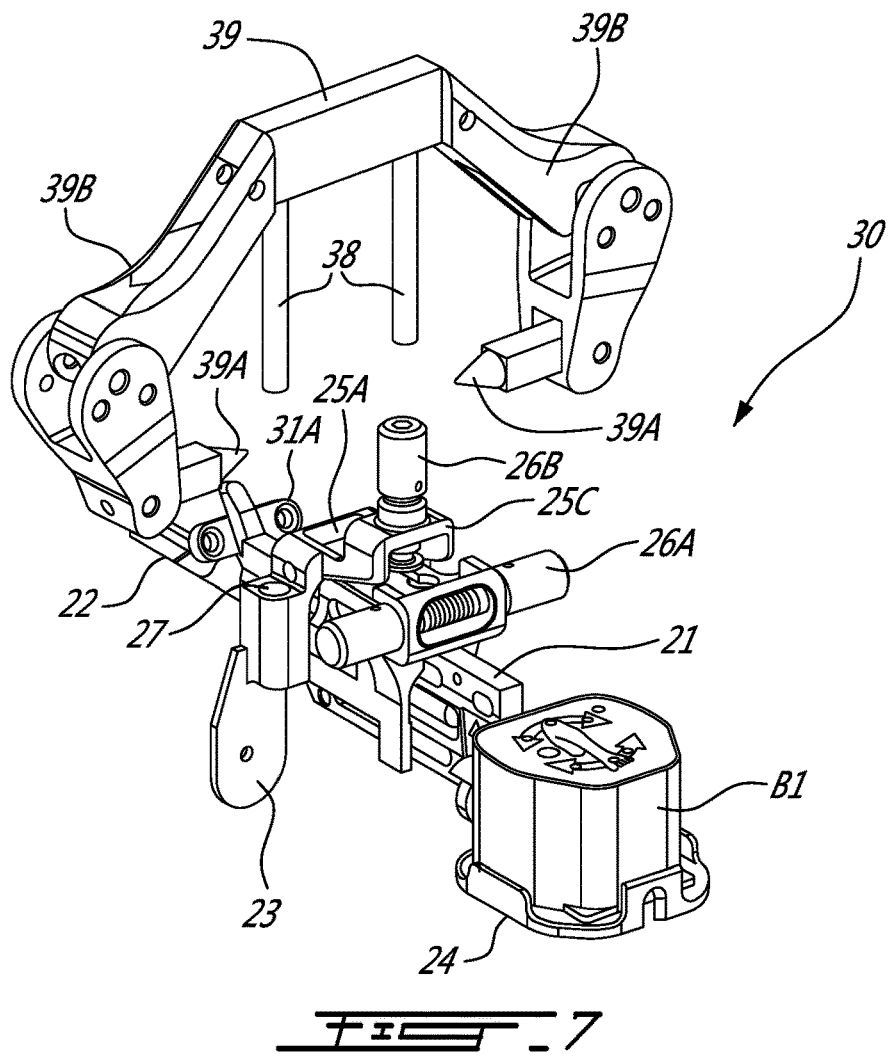
FIG. 7 is an assembly view of the knee reference jig of FIG. 6.
Figure 8:
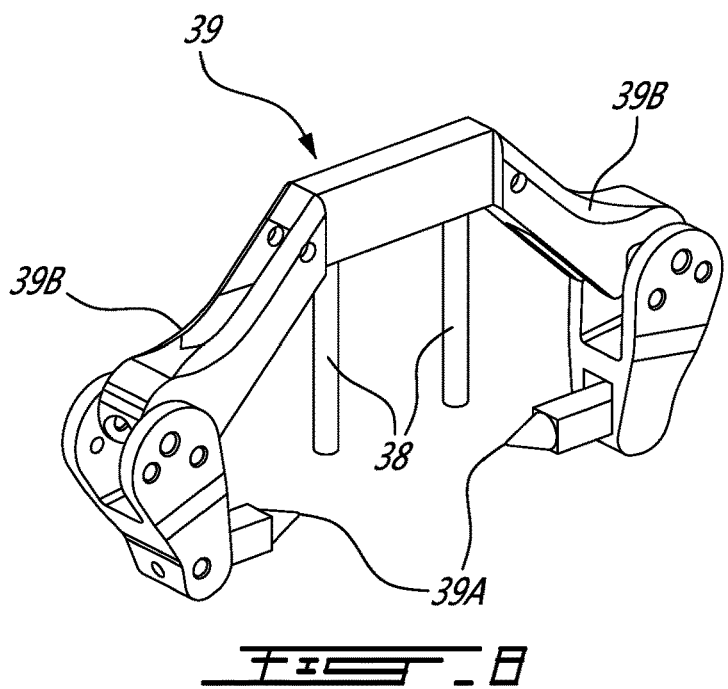
FIG. 8 is a perspective view of jaw of the knee reference jig of FIG. 6.

Referring to FIGS. 6-8, the knee reference jig 30 is shown in greater detail, and is used as an alternative to the knee reference jig 20. However, the reference jigs 20 and 30 share components, whereby like reference numerals will refer to like components. The knee reference jig 30 is configured to orient itself with the medial and lateral prominences of the epicondyles, and is therefore used if the operator selects transepicondylar line alignment. The jig 30 has a base 21 that defines the structure of the jig 30, as the base 21 supports other components of the jig 30. A pin 22 projects from the base 21, and is sized so as to be received in a hole drilled in the distal femur at the mechanical axis entry point. Therefore, when the pin 22 is in the drilled hole, the jig 30 is at the mechanical axis entry point. The base 21 has an abutment plane, herein shown as a pair of abutment surfaces 23, though one or more of the abutment surfaces 23 may be present. The abutment surfaces 23 abut against the distal surfaces of the condyles (i.e., medial and lateral condyles) when the pin 22 is received in the drilled hole. The base 21 also has a receptacle 24, for receiving the inertial sensor unit B1. The receptacle 24 is shaped for receiving the inertial sensor unit B1, such that any preset virtual orientation or like calibration data programmed into the inertial sensor unit B1 is aligned with physical parts of the jig 30, such as the abutment plane and the pin 22.

An adjustment mechanism 25 is also connected to the base 21 and is also configured to support the cut block 40, with rotational movements of the bracket 25C about pivots 25A and 25B being controllable by the knobs 26A and 26B, respectively. The bracket 25C is therefore displaceable in two rotational DOFs relative to the base 21, such as a rotation about the AP axis, and a rotation about the ML axis. The knobs 26A and 26B allow minute or micro orientation adjustments.

The jig 30 differs from the jig 20 in that the landmark alignment unit is different. The base 21 may further define a pair of parallel slots 27 for slidingly receiving rails 38, in a translational DOF. An epicondylar jaw 39 is a landmark alignment unit supported by the rails 38, such that the jaw 39 may be brought closer or further to the base 31. The jaw 39 has bone alignment components in the form of ends, such as pointy ends 39A, at the tip of articulated arms 39B moving in a plane parallel to the abutment plane of the jig 30. The ends 39A are configured to come into contact with the prominences of the medial and lateral epicondyles, with the ends 39A remaining collinear throughout movement of the articular arms 39B. There is a space of gap between the ends 39A for receiving the bone between, with a line passing through the ends being generally parallel to the abutment plane of the abutment surface 23. The line is used to be coincident with the transepicondylar line or other bone landmark.

Securing the knee reference jig 30 to the distal femur according to 11 of FIG. 1 entails inserting the pin 32 in the hole drilled at the mechanical axis entry point, and adjusting the penetration until the abutment plane of the base 21 is against at least one of the distal aspects of the condyles. In an embodiment, the jig 30 is manually oriented such that the ends 39A of the jaw 39 are aligned with the transepicondylar line from an end point of view (i.e., located on the cranial-caudal axis). The base 21 may then be driven into the hole of the femur 20, with the penetration adjusted until the abutment plane of the base 21 is against at least one of the distal aspects of the condyles. Setting the orientation as in 12 of FIG. 1 may hence require rotating the base 21 on itself, and the jaw 39 is translated and articulated arms 39B are displaced for the ends 39B to be aligned with the prominences of the medial and lateral epicondyles from the cranial-caudal point of view. The knee reference jig 30 is thus oriented with the transepicondylar line, and may be driven into to the femur to be fixed by way of the spike 22, though other fixation means could be used such as pins, screws, etc, as applicable to the jig 20 as well. The femoral coordinate system may hence be created by the appropriate kinematics as described in 13 of the method 10, using the inertial sensor unit B1 on the jig 30, using the known geometry between the inertial sensor unit B1 and the preset virtual calibration in the inertial sensor unit B1. The jaw 39 may then be removed to navigate the orientation of the cut block 40, using the knobs 26A and 26B.

In FIG. 7, there is also shown a front tab 31A projecting from the base 21. The front tab 31A could be used as an alternative to the jaw 39 to align the base 31 with Whiteside's line. The use of the jig 30 with the tab 21A is similar to the use of the jig 30 with the jaw 39, with the base 21 being rotated on itself to align the tab 31A with Whiteside's line, prior to being driven or secured to the femur, via the spike 22 or equivalent fastener.

Referring to FIG. 9, the cut block 40 is shown as pinned to the femur, after the distal cut has been performed, and thus after 14 and 15 in the method 10. The cut block 40 defines a cut slot 41 devised to receive a flat saw blade, although other configurations are also contemplated. The cut slot 41 may therefore be aligned with a cut plane of the cut block 40. The cut block 40 also defines numerous guide channels for pins 42 to anchor the cut block 40 to the distal femur once the cut block 40 is in a desired orientation, after navigation when connected to either one of the reference jigs 20 and 30, as described above. To navigate the cut block 40 according to 14 in the method 10, the cut block 40 has a support arm 43 with a receptacle 44 for receiving the inertial sensor unit B2. The receptacle 44 is shaped for receiving the inertial sensor unit B2 in a predetermined and planned arrangement, such that any preset virtual orientation or like calibration data programmed into the inertial sensor unit B2 is aligned with physical parts of the cut block 40, such as the cut plane and cut slot 41. During navigation as per 14, the cut block 40 is attached to the bracket 25C or any other component of the jig 20/30 moving relative to the base 21, with a link (not shown) taking into account a thickness of the implant. The adjustment mechanism 25 is at a zero setting, i.e., a baseline setting, due to steps taken to orient the adjustment mechanism with the landmarks of the femur, such as the distal aspects of the condyles, and any of Whiteside's line, posterior plane of the condyles, and/or transepicondylar axis, etc. The knobs 26 of the jigs 20/30 are manually actuated to adjust two rotational DOFs of the adjustment mechanism 25, resulting in varus-valgus and/or flexion-extension adjustment for the cut plane of the cut block 40, with reference to the baseline settings. The cut block 40, with the concurrent readings of both inertial sensor units B1 and B2 enabling the real-time calculation of the orientation of the cut plane of the cut block 40 in the femoral coordinate system. The orientation may be expressed in any appropriate terms, such as varus-valgus, flexion-extension, etc. Once the cut block 40 is fixed with the pins 42 to the femur in the manner shown in FIG. 9, the knee reference jigs 20/30 may be removed for the distal cut to be performed, as in 15 of method 10. The inertial sensor unit B2 then becomes the unit responsible for tracking the femoral coordinate system.

According to an embodiment, there is no inertial sensor unit B1 on the reference jigs 20 and 30, the system using instead the zero setting to record an orientation of the mechanical axis in the inertial sensor unit B2, with appropriate kinematics as described above. Then, the femur is kept in a fixed orientation while data from the inertial sensor unit B2 during movements of the cut block 40 as connected to the adjustment mechanism 25 is used to determine varus-valgus and flexion-extension relative to the fixed mechanical axis.

Figure 10:
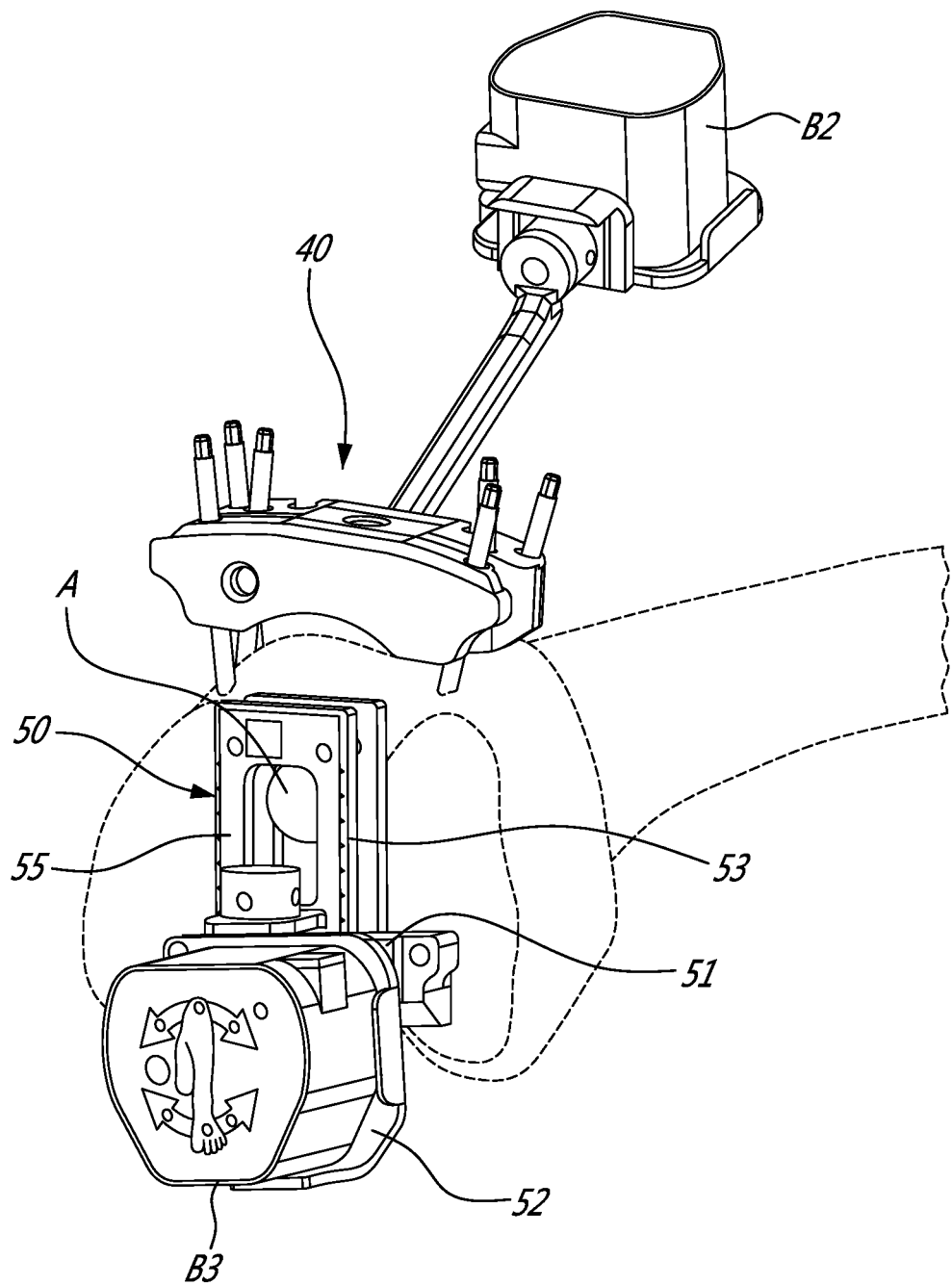
FIG. 10 is a perspective view of a cutting guide in accordance with another embodiment of the present disclosure, as validating a distal cut.
Figure 11:
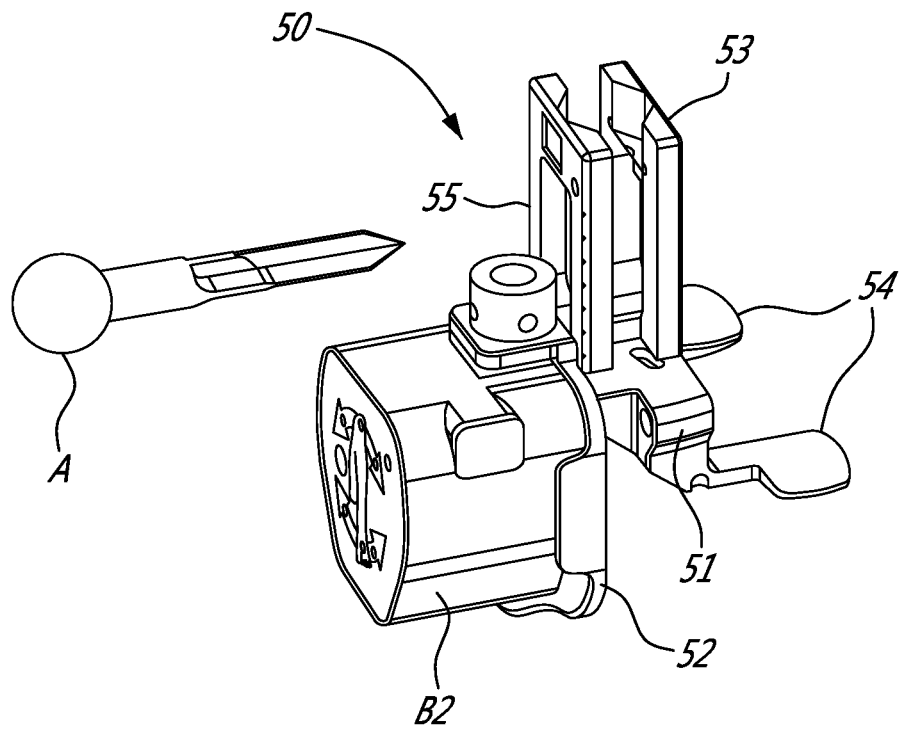
FIG. 11 is a perspective view of the cutting guide of FIG. 9, as detached from the femur.
Figure 12:
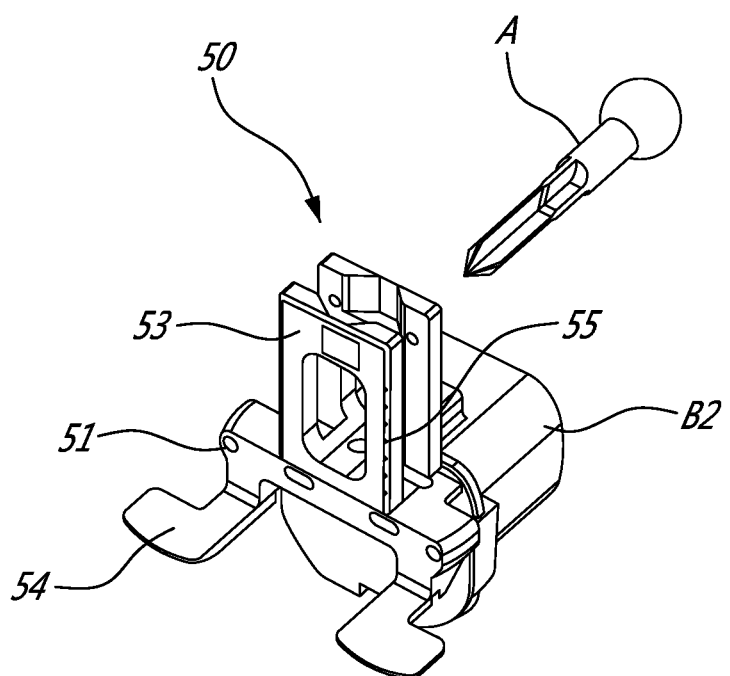
FIG. 12 is another perspective view of the cutting guide of FIG. 9, as detached from the femur.

Referring to FIGS. 10-12, the cut guide 50 is shown in a configuration for validating the distal cut, as in 16 of the method 10. The cut guide 50 may be used with the pin A with ball head or like bone anchor, inserted at the mechanical axis entry point, after resection with the guiding assistance of the cut block 40. The cut guide 50 has a base 51 that has a flat underside (a.k.a., sliding plane), for being laid onto the plane of the distal cut as shown in FIG. 10. The base 51 may also have a receptacle 52. The receptacle 52 is shaped for receiving inertial sensor unit B3 in a predetermined and planned arrangement taking into consideration the geometry of the cut guide 50 and the spatial relation between the receptacle 52 and the sliding plane, such that any preset virtual orientation or like calibration data programmed into the inertial sensor unit B3 is aligned with physical parts of the cut guide 50, such as the plane of the flat underside, a medio-lateral axis and/or anterior-posterior axis of the cut guide 50, and/or a condylar abutment plane as described hereinafter. The flat underside may be defined by a rack 53, adapted to house the ball head of the pin A and hence form a rotational and translational joint. As an alternative embodiment, the ball may be on the cut guide 50, and a socket operatively receiving the ball A may be secured to the bone. When the flat underside of the base 51 is laid on the distal cut plane and the base 51 is slid on the distal cut plane—the distal cut plane and the abutment plane being coplanar —, the cut guide 50 is constrained into moving in a single rotational DOF, i.e., one about an axis generally parallel to the mechanical axis. Accordingly, the combined readings of the inertial sensor units B2 and B3 may be used by the CAS system in order to determine the orientation of the distal cut plane relative to the femoral coordinate system—tracked by the inertial sensor unit B2. In an embodiment, the femur is fixed, and only the inertial sensor unit B3 is used. In such a scenario, the inertial sensor unit B2 may be removed from the cut block 40 and be installed in the cut guide 50, via dead reckoning.

The cut guide 50 may also be used in a navigation of the distal cut plane as per 17 of method 10, in order to prepare further alterations to the distal femur, as in 18 of the method 10. The components attached to the cut guide 50 may be dependent on the type of alignment desired by the operator. As shown in FIGS. 11 and 12, the cut guide 50 may for example have a condylar abutment 54 transversely positioned at the end of the base 51. In similar fashion to the jig 20, the condylar abutment 54 defines a condylar plane, configured to come into contact with posterior aspects of the medial and lateral condyles, for posterior referencing. The condylar plane serves as a reference plane in knee arthroplasty, whereby the presence of the condylar abutment 54 allows alignment of the cut guide 50 with the condylar plane, after the orientation of the distal cut plane has been validated in the femoral coordinate system. This may for instance be used if the reference jig 30 was selected for alignment with the transepicondylar line. The condylar abutment 54 may introduce a reference to the condylar plane to the procedure. In an embodiment in which the reference jig 20 is used, the condylar abutment 54 could confirm that the procedure up to that point is aligned with the initial alignment using the condylar abutment 29 (FIGS. 2-5).

The joint concurrently formed by the rack 53 and the ball head of the pin A allows movements of the cut guide 50 so that it may come into contact with the posterior aspects of the medial and lateral condyles. The rack 53 may also have a scale 55. The scale 55 may be used with an add-on sizing bracket 60, to determine the size of the femoral component or implant in the anterior-posterior direction.

Figure 13:
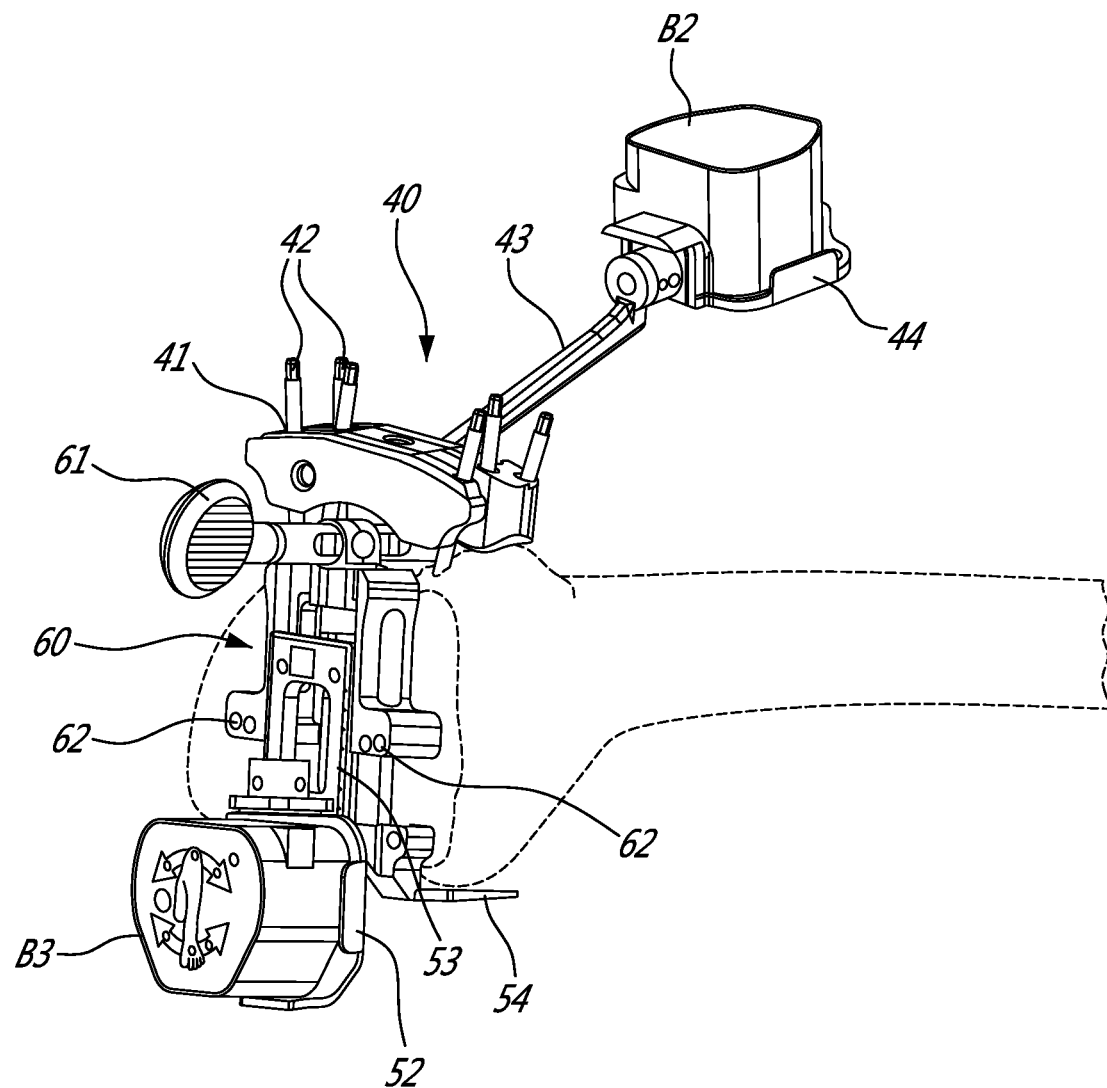
FIG. 13 is a perspective view of the cutting guide of FIG. 12, with a sizing bracket.

Referring to FIG. 13, the cut guide 50 is shown with its bracket 60. The bracket 60 is connected to the rack 53 to form a translational joint having a direction parallel to the distal cut plane when the cut guide 50 is laid onto the distal cut plane. The bracket 60 supports a sizing boom 61 configured to be received in the patellofemoral groove, as in FIG. 13. The bracket 60 has pointing marks aligned with the scale 55, in order to indicate the size of the distal cut of the femur in the anterior-posterior direction. The measurement may be obtained when the sizing boom 61 is in the patellofemoral groove on the anterior cortex while the condylar abutment 54 is in abutment with the posterior aspects of the medial and lateral condyles. Drill guide holes 62 are defined in extensions of the bracket 60. The drill guide holes 62 are provided to place pins in the distal femur, which pins serve as guiding landmarks for any subsequent tool to be placed against the distal cut for the further alterations to be made to the femur, as in 18 of the method 10.

Consequently, the reference jigs 20 and 30 physically position and orient the method 10 with bone landmarks, and the method 10 may then perform its subsequent steps based on the original alignment. The cut block 40, the cut guide 50 and the bracket 60 are positioned and orientation in continuation with the original alignment, using appropriate sensors such as the inertial sensor units B1, B2 and/or B3. As mentioned above, B1, B2 and B3 may be a single inertial sensor unit, moved from device to device.

The inertial sensor units B1, B2 and B3 include one or more inertial sensors, a transmitter (or like communication circuitry, such as a wireless transmitter, a transceiver or the like), and may support optional confirmation indicator or displays. If more than one inertial sensor unit is used, the inertial sensor units communicate with one another to share tracking data and share the femoral coordinate system. In an embodiment of the present disclosure, the inertial sensor may be an accelerometer providing two rotational degrees of freedom (e.g., inertial sensor unit B3), and may include other types of sensors, such as gyroscopes (B1). Examples of suitable devices used as tracking circuitry 20 are the capacitive accelerometer sensor (CAPAS), electrolytic tilt sensors and the tri-axis sensor (TAS), amongst other possibilities. The CAPAS provides a 2-axis measurement of the acceleration (e.g., g force) of an object by being fixed thereto.

In the active state of the inertial sensor units B1-B3, variations of the acceleration are reflective of a modification in the orientation of the inertial sensor unit B1-B3. The output of any of the inertial sensor unit B1-B3 is a 2-axis relative angular value or 3-axis if the inertial sensor unit 12 is calibrated. Therefore, the inertial sensor units provides real-time orientation data for the femur.

The transmitter transmits the tracking data of the to the processing system of the CAS system, if present, or communicates the tracking data to the other inertial sensor units. The transmission of data may be wireless, or through wired connection. The technology used for the transmitter may be selected to operate in a surgical environment, such as RF. As an example, Bluetooth™, Zigbee™ or Wi-Fi transmitters are considered for their wide availability and allow the integration of the trackable member to surgical instruments. The trackable member can be manufactured as a single disposable unit, possibly integrated to implant instrumentation (e.g. a disposable, self-trackable cutting guide for TKR). As an alternative embodiment, sensors can be configured to communicate necessary information between themselves.

Another feature considered for the inertial sensor units is the confirmation indicator or display that provides data to the operator or surgeon. For instance, indications about a suitable position/orientation of the surgical tool may be provided directly on the tool, so as to facilitate the procedure for the surgeon/operator handling the tool. The confirmation indicator is circuitry with on/off LEDs (e.g., red and a green LEDs) or another suitable form of compact electronic display responsive to signals or commands received from the CAS system.

The inertial sensor units B1, B2 and B3 are part of the CAS system, which may or may not have a processing unit. The inertial sensor units B1, B2 and B3 may be programmed with calibration data (i.e., virtual preset orientation) and may have sufficient computing capacity to perform all CAS functions described above.

The above description makes reference to the femur. It is however contemplated to use the reference jigs 20 and 30, the cut block 40 and the cut guide 50 with other bones, including the tibia, for instance to guide the resection of the tibial plateau.

The invention claimed is:

1. A system for validating a distal cut of a femur comprising:
    a processor unit; and
    a non-transitory computer-readable memory communicatively coupled to the processing unit and comprising computer-readable program instructions executable by the processing unit for:
    tracking a femoral coordinate system with a first inertial sensor unit of a computer-assisted surgery (CAS) system secured to the femur,
    receiving readings of a second inertial sensor unit of the computer-assisted surgery (CAS) system as supported by a guide coplanar against the distal cut,
    receiving readings of an inertial sensor unit of the computer-assisted surgery (CAS) as supported by another guide, the other guide against posterior condyles, whereby tracking the femoral coordinate system includes tracking posterior condylar plane,
    determining an orientation of a plane of the distal cut in the femoral coordinate system, and
    validating the orientation with a planned orientation of the distal cut.

2. The system according to claim 1, wherein tracking a femoral coordinate system includes tracking the femoral coordinate system with the first inertial sensor oriented relative to distal aspects of the femur.

3. The system according to claim 1, wherein tracking a femoral coordinate system includes tracking the femoral coordinate system as including a transepicondylar line of the femur.

4. The system according to claim 1, further including receiving readings of an inertial sensor unit of the computer-assisted surgery (CAS) as supported by another guide, the other guide against a plane of a posterior cut, after resection.

5. The system according to claim 4, further including determining an orientation of the plane of the posterior cut in the femoral coordinate system.

6. The system according to claim 5, further including validating the orientation of the plane of the posterior cut with a planned orientation of the posterior cut.

* * * * *